(12) United States Patent
Li et al.

(10) Patent No.: US 10,551,313 B1
(45) Date of Patent: Feb. 4, 2020

(54) SURFACE PLASMON RESONANCE BASED MECHANICAL SENSING OF BEATING HEART CELLS

(71) Applicants: Chenzhong Li, Miami, FL (US); Maedeh Mozneb, Doral, FL (US); Amirali Nilchian, Davie, FL (US)

(72) Inventors: Chenzhong Li, Miami, FL (US); Maedeh Mozneb, Doral, FL (US); Amirali Nilchian, Davie, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 16/383,723

(22) Filed: Apr. 15, 2019

(51) Int. Cl.
   G01N 21/59 (2006.01)
   G01N 33/483 (2006.01)

(52) U.S. Cl.
   CPC ......... *G01N 21/59* (2013.01); *G01N 33/4833* (2013.01); *G01N 2021/5903* (2013.01); *G01N 2201/0446* (2013.01)

(58) Field of Classification Search
   CPC .............. G01N 21/59; G01N 33/4833; G01N 2021/5903; G01N 2201/0446
   USPC ......................................................... 356/445
   See application file for complete search history.

(56) References Cited

U.S. PATENT DOCUMENTS

| | | | | |
|---|---|---|---|---|
| 4,997,278 A * | 3/1991 | Finlan | ................ | G01N 21/553 356/128 |
| 5,327,225 A * | 7/1994 | Bender | ................ | G01N 21/553 250/307 |
| 5,374,563 A * | 12/1994 | Maule | ................ | G01N 21/553 356/318 |
| 5,875,032 A * | 2/1999 | Naya | ................ | G01N 21/553 356/445 |
| 7,037,727 B1 * | 5/2006 | Miura | ................ | G01N 21/553 385/12 |
| 7,619,724 B2 * | 11/2009 | Martinez | ................ | G01N 21/553 356/128 |
| 7,879,619 B2 * | 2/2011 | Jing | ................ | G01N 21/553 250/573 |
| 8,263,387 B2 * | 9/2012 | Pagano | ................ | B01L 3/502761 422/527 |
| 8,587,786 B2 * | 11/2013 | Zybin | ................ | G01N 15/1463 356/445 |
| 9,207,173 B2 * | 12/2015 | Li | ................ | G01N 21/553 |

(Continued)

OTHER PUBLICATIONS

Zhang et al., "High-Throughput Assessment of Drug Cardiac Safety Using a High-Speed Impedance Detection Technology-Based Heart-on-a-Chip", MDPI Journal, Micromachines, 2016, vol. 7, Issue 7, Article No. 122, 9 sheets.

*Primary Examiner* — Roy M Punnoose
(74) *Attorney, Agent, or Firm* — Saliwanchik, Lloyd & Eisenschenk

(57) ABSTRACT

Surface plasmon resonance (SPR) based sensing systems and methods for sensing rhythmic beating characteristics of living cells are provided. An SPR based sensing system can include: an SPR sensing surface capable of generating SPR upon stimulation by incident light and configured to sense contractions, expansions, and/or movements of a plurality of living cells on the SPR sensing surface; and a cell culture module for culturing the living cells on the SPR sensing surface. In addition, the SPR based sensing system can perform a real-time analysis of one or more analytes secreted from the living cells by including a coating on the SPR sensing surface.

19 Claims, 6 Drawing Sheets

(56) References Cited

U.S. PATENT DOCUMENTS

| | | | |
|---|---|---|---|
| 9,465,028 B2* | 10/2016 | Li | G01N 21/553 |
| 9,752,982 B2* | 9/2017 | Echtermeyer | G01N 21/554 |
| 2002/0009812 A1* | 1/2002 | Miura | G01N 21/553 |
| | | | 436/518 |
| 2006/0109472 A1* | 5/2006 | Muraishi | G01N 21/553 |
| | | | 356/445 |
| 2006/0119852 A1* | 6/2006 | Shimizu | G01N 21/05 |
| | | | 356/445 |
| 2008/0130004 A1* | 6/2008 | Pyo | G01N 21/553 |
| | | | 356/445 |
| 2008/0273207 A1* | 11/2008 | Sekiguchi | G01N 21/3581 |
| | | | 356/445 |
| 2009/0213383 A1* | 8/2009 | Ly | G01N 21/553 |
| | | | 356/445 |
| 2011/0188043 A1* | 8/2011 | Davidov | G01N 21/553 |
| | | | 356/445 |
| 2012/0133943 A1* | 5/2012 | Fontaine | G01N 21/553 |
| | | | 356/445 |
| 2014/0268159 A1* | 9/2014 | Li | G01N 21/553 |
| | | | 356/445 |

* cited by examiner

SURFACE PLASMON RESONANCE BASED MECHANICAL SENSING OF BEATING HEART CELLS

GOVERNMENT SUPPORT

This invention was made with government support under EEC-1647837 awarded by National Science Foundation. The government has certain rights in the invention.

BACKGROUND

In vitro measurements of cardiomyocyte contractility have been investigated for determining physiological consequence of various genetic manipulations and identifying potential therapeutic targets for the treatment of heart failure. Most recent technologies in analysis of heart tissue viability, and more specifically contractibility, adopt cumbersome tactics engaging micro pillars, nano pillars, or cantilevers in order to detect mechanical movement of the living cells. However, these technologies are not only time consuming, but also expensive and labor-intensive.

Moreover, determining viability and strength of the contraction of living cells by analyzing kinetic properties of biomarkers released by the living cells has attracted more and more investigations. Nevertheless, these mechanical and chemical analyses were mostly performed by microfluidic devices with embedded sensors which require time-consuming operation procedures and complicated trainings of the operators.

BRIEF SUMMARY

There continues to be a need in the art for improved designs and techniques for a sensing system and methods for detecting kinetic properties of living cells.

Embodiments of the subject invention pertain to surface plasmon resonance (SPR) based sensing systems and methods for sensing contractions, expansions, or movements of living cells. An SPR based sensing system can comprise: an SPR sensing surface capable of generating (and configured to generate) SPR upon stimulation by incident light and configured to sense contractions, expansions, or movements of a plurality of living cells on the SPR sensing surface; and a cell culture module configured to culture the living cells on the SPR sensing surface.

In an embodiment, an SPR based sensing system for sensing contractions, expansions, movements, or a combination thereof of living cells can comprise: an SPR sensing surface configured to generate SPR upon stimulation by incident light and configured to sense contractions, expansions, movements, or a combination thereof of the living cells on the SPR sensing surface; and at least one cell culture module configured to culture the living cells to be disposed on the SPR sensing surface.

In another embodiment, a method of sensing contractibility, movements, or both of living cells can comprise using an SPR based sensing system that comprises: an SPR sensing surface configured to generate SPR upon stimulation by incident light; and at least one cell culture module for culturing the living cells. The method can further comprise: culturing, by the at least one cell culture module, the living cells to be disposed on the SPR sensing surface; and sensing, by the SPR sensing surface, contractions, expansions, movements, or a combination thereof of the living cells.

In another embodiment, an SPR based sensing system for sensing contractions, expansions, movements, or a combination thereof of living cells can comprise: an SPR sensing surface configured to generate SPR upon stimulation by incident light and configured to sense contractions, expansions, movements, or a combination thereof of the living cells on the SPR sensing surface; at least one cell culture module configured to culture the living cells to be disposed on the SPR sensing surface; a support layer capable of transmitting light, the SPR sensing surface being adhered to the support layer; a concentrator configured to determine an optimal concentration of the living cells cultured on the SPR sensing surface for sensing contractions, expansions, movements, or a combination thereof of the living cells; and at least one controller. The at least one controller can be configured to determine both: an optimal flow rate of a culture medium contacting the living cells cultured on the SPR sensing surface for sensing contractions, expansions, movements, or a combination thereof of the living cells; and an optimal cell culturing condition of the at least one cell culture module for sensing contractions, expansions, movements, or a combination thereof of the living cells. That is, at least one controller can be configured to determine the optimal flow rate of the culture medium, and at least one separate controller can be configured to determine the optimal cell culturing condition of the at least one cell culture module; or there can be partial or complete overlap between the at least one controller configured to determine the optimal flow rate of the culture medium and the at least one controller configured to determine the optimal cell culturing condition of the at least one cell culture module. The SPR sensing surface can comprise a metallic surface (e.g., comprising gold), and the living cells can comprise living cardiomyocytes. The system can be configured for real-time analysis of at least one analyte secreted from the living cells, and the system can comprise a coating coated on the SPR sensing surface for performing real-time analysis of the at least one analyte secreted from the living cells. The at least one cell culture module can be configured such that the at least one analyte secreted from the living cells is released onto the SPR sensing surface to be sensed by the SPR sensing surface, and the coating can comprise a binding partner that binds to the at least one analyte secreted from the living cells, the binding partner being configured to bind specifically to a biomarker.

BRIEF DESCRIPTION OF DRAWINGS

Referring to FIG. 6A, an SPR sensor chip (e.g., a gold SPR sensor chip) and cell concentrator (e.g., a PDMS cell concentrator such as the generally circular concentrator shown in FIG. 3) can be used with a plate, such as a 6-well plate. Any number of wells, such as all six wells, can include a respective SPR sensor chip and cell concentrator. FIG. 6B shows a vessel (top-right) that can provide cell cultures and a 6-well plate (bottom-right) with each well having a respective SPR sensor chip and cell concentrator. The cell cultures can be added to the SPR sensor chip in each well of the plate by adding to the well through the cell concentrator on the SPR sensor chip.

DETAILED DESCRIPTION

Embodiments of the subject invention pertain to surface plasmon resonance (SPR) based sensing systems and methods for sensing contractions, expansions, or movements of living cells. An SPR based sensing system can comprise: an SPR sensing surface capable of generating (and configured to generate) SPR upon stimulation by incident light and configured to sense contractions, expansions, or movements of a plurality of living cells on the SPR sensing surface; and a cell culture module configured to culture the living cells on the SPR sensing surface.

SPR is a useful biosensing technique to identify characteristics of living cells and analysis of biomarker secretion from living cells. SPR is the resonance of the electron charge density wave (plasmons) generated at the interface of a conductive metal (e.g., gold) and medium (any fluid flow) when excited by polarized light. Any mass changes on the surface of the conductive metal result in a change in the reflected light known as a resonance angle.

When the terms "on" or "over" are used herein, when referring to layers, regions, patterns, or structures, it is understood that the layer, region, pattern or structure can be directly on another layer or structure, or intervening layers, regions, patterns, or structures may also be present. When the terms "under" or "below" are used herein, when referring to layers, regions, patterns, or structures, it is understood that the layer, region, pattern or structure can be directly under the other layer or structure, or intervening layers, regions, patterns, or structures may also be present. When the term "directly on" is used herein, when referring to layers, regions, patterns, or structures, it is understood that the layer, region, pattern or structure is directly on another layer or structure, such that no intervening layers, regions, patterns, or structures are present. When the term "direct contact" is used herein, when referring to layers, regions, patterns, or structures in contact with other layers, regions, patterns, or structures, it is understood that the layer, region, pattern or structure is in direct, physical contact with the other layer, region, pattern, or structure, such that no intervening layers, regions, patterns, or structures are present.

When the term "approximately" or "about" is used herein, in conjunction with a numerical value, it is understood that the value can be in a range of 90% of the value to 110% of the value, i.e. the value can be +/−10% of the stated value. For example, "about 1 kg" means from 0.90 kg to 1.1.

Figure 1A:
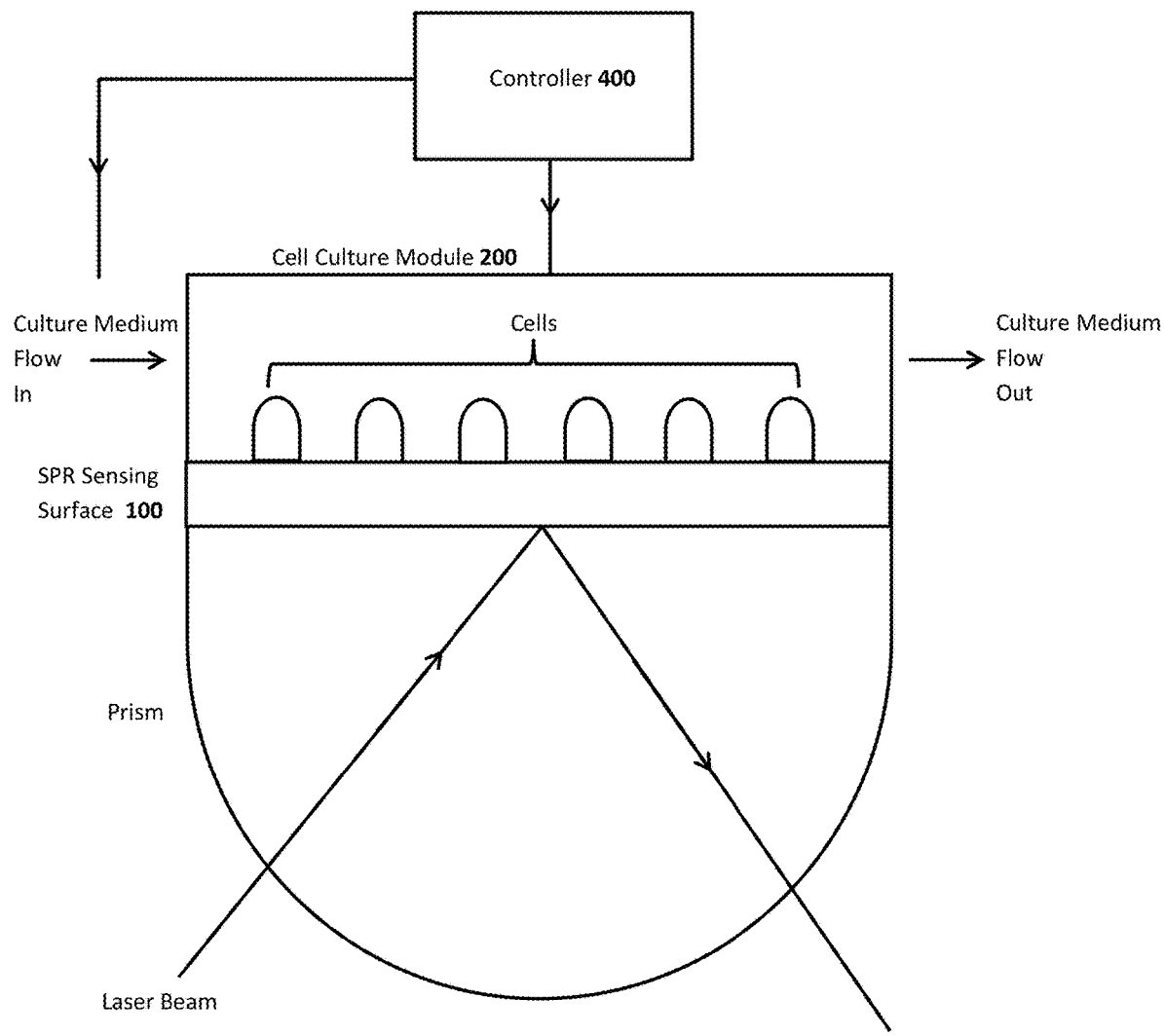
FIG. 1(a) is a schematic diagram of a surface plasmon resonance (SPR) based sensing system for sensing contractions, expansions, or movements of living cells, according to an embodiment of the subject invention.

FIG. 1(a) is a schematic diagram of an SPR based sensing system according to an embodiment of the subject invention. The SPR based sensing system can comprise: an SPR sensing surface 100 capable of generating (and configured to generate) SPR upon stimulation by incident light and configured to sense contractions, expansions, or movements of a plurality of living cells on the SPR sensing surface 100; and at least one cell culture module 200 configured to culture the living cells on the SPR sensing surface 100.

In an embodiment, the SPR sensing surface 100 can comprise a metallic surface including, but not limited to, gold, silver, copper, platinum, aluminum, tin, zinc, tantalum, magnesium, nickel, palladium, cobalt, molybdenum, iron, titanium, chromium, and alloys comprising two or more aforementioned metals. In an embodiment, the metallic surface can comprise a thin (e.g., thickness of 60 nm or less) metal layer (e.g., a metal layer with a thickness of 45 nm). In an embodiment, the metallic surface can comprise gold, such as a thin (e.g., 60 nm or less) layer of gold. For example, the metallic surface can comprise a thin layer of gold having a thickness of 45 nm.

In an embodiment, the SPR based sensing system can further comprise a light source configured to illuminate the SPR sensing surface. The term "light," as used herein, includes visible and non-visible light. The light source can emit light including, for example, violet, blue, green, yellow, orange, red, far-red, ultraviolet light (such as ultraviolet A, ultraviolet B, ultraviolet C), X-rays, and/or infrared spectral ranges.

Light sources for illuminating the SPR sensing surface can include, but are not limited to: laser light sources, such as helium neon laser or other suitable lasers; an incandescent light; a light emitting diode (LED); an organic light-emitting diode (OLED); an organic luminescent diode; a light oscillator; a light source configured to emit a filtered, collimated light; and a light source configured to emit a monochromatic light.

In certain embodiments, the light source can comprise a light polarization control means. Suitable light polarization control means include, but are not limited to, polaroid, Glan prism, polarizing beam splitter, or any combination thereof.

In an embodiment, the SPR based sensing system can further comprise an optical detector for measuring the reflectivity of the light by the SPR sensing surface.

In an embodiment, the SPR based system can further comprise, or be connected to, a controller, a processor, a computer processing system, a server, and/or a network. In certain embodiments, the controller, the processor, the computer process system, the server, the network, or some combination thereof can perform functions including, but not limited to, controlling the output of the light source, measuring the reflectivity of the light detected by the detector, transmitting and/or processing data, and/or performing data analysis.

In an embodiment, the controller, the processor, the computer processing system, the server, or the network can comprise software code that can be stored on one or more computer-readable media (e.g., non-transitory computer-readable media). When a data-processing system or apparatus reads and executes the code and/or data stored on a machine-readable medium, the data-processing system or apparatus system performs the methods and processes embodied as the software code stored within the machine-readable medium.

In an embodiment, an array can be provided comprising multiple SPR based sensing systems as described herein. For example, an array of six SPR based sensing systems can be cultured with rat cardiomyocytes and the beating characteristics of the rat cardiomyocytes can be monitored by the SPR array in any suitable manner.

Referring to FIG. 1(a), the SPR based sensing system can comprise at least one cell culture module 200. In an embodiment, the cell culture module 200 can be mounted on the SPR sensing surface 100. In another embodiment, the cell culture module 200 can be mounted above the SPR sensing surface 100.

In an embodiment, the cell culture module 200 can comprise a carrier for supporting the living cells. In an embodiment, the cell culture module 200, which comprises the carrier for supporting the living cells, can be controllably sealed to hold the living cells in its inner space.

In certain embodiments, the cell culture module 200 can comprise, or be connected to, one or more controllers 400 configured to control cell culture conditions of the cell culture module 200, such as flow rates of culture medium, temperature, humidity, gas exchange, pH, $CO_2$ level, $O_2$ level, pressure, and/or light. In certain embodiments, the cell culture module 200 can comprise one or more sensors configured to detect factors, such as cell viability, cell count, cell concentration, cell activity, cell metabolite level, level of nutrients, flow rates of culture medium, temperature, humidity, gas exchange, pH, $CO_2$ level, $O_2$ level, pressure, and/or light.

In certain embodiments, the cell culture module 200 can further comprise one or more pumps, valves, and/or flow channels to provide a constant inflow of gas and/or fluids, such as culture medium, water, buffers, analytes, nutrients, and/or washes. In another embodiment, the cell culture module 200 can further comprise one or more fluid circulation channels. In an embodiment, the fluid circulation channel fills fluids into the inner space of the cell culture module and circulates the gas and/or liquid. In an embodiment, the fluid circulation channel is configured to provide unidirectional flow of gas and/or liquid.

The carrier for supporting the living cells and/or the cell culture module 200 can be made of, or comprise, materials including, but not limited to, polydimethylsiloxane (PDMS), glass ceramics, glass, ceramics, silica, Mania, zirconia, alumina, hydroxyapatite, metal oxides, and a combination thereof.

The term "culturing," as used herein, refers to incubating a cell and/or microorganism or a plurality thereof under conditions wherein the cell and/or microorganism or plurality thereof can perform some, if not all, biological processes, such as, for example, tissue expansions, tissue contractions, tissue movements, growth, reproduction, transcription, translation, and metabolism.

In one particular embodiment, rat cardiomyocytes were isolated from neonatal rat hearts from day one through day three and cultured on the SPR sensing surface 100 of the SPR based sensing system. Subsequently, the spontaneous contractions, expansions, or movements of the rat cardiomyocytes under normal living conditions were monitored by using the SPR based sensing system.

In an embodiment, the cultured living cells (for example, cardiomyocytes) on the SPR sensing surface are monitored to observe the changes in SPR resonance angle and the effect of beating cells on the SPR based sensing system over time.

In an embodiment, the viability and strength of the expansions, contractions, or movements of the cells are analyzed in real time by using the SPR based sensing system.

In an embodiment, the effects of certain drugs on cardiomyocytes and their toxicity to the cells are monitored by using the cell cultured on and/or integrated with the SPR sensing surface. If the beating decreases with inducing a drug that is toxic to the cardiomyocytes, the SPR response goes down in amplitude, showing lower contractability of the cells.

In an embodiment, by using the space of the cell culture module 200 on top of the SPR sensing surface 100, a three-dimensional (3D) cell structure can be cultured on the the SPR sensing surface to monitor the effects of a three-dimensional (3D) tissue culture.

In an embodiment, with specific coating techniques, a real-time kinetic analysis of biomarkers released by the living cells can be performed by the the SPR sensing surface 100 of embodiments of the subject invention.

Figure 1B:
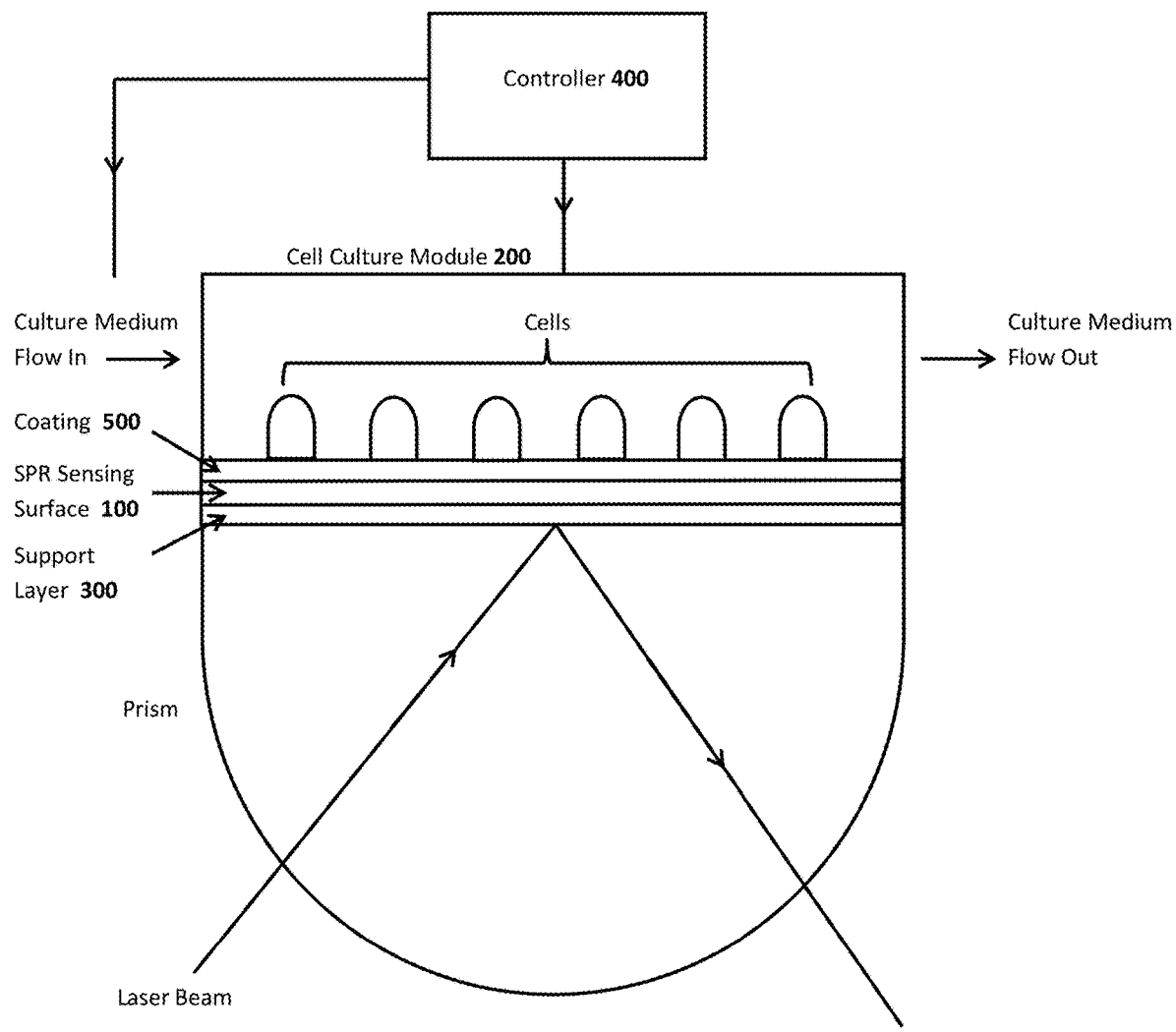
FIG. 1(b) is a schematic diagram of an SPR based sensing system having a coating for real-time kinetic analysis of biomarkers released by the living cells, according to an embodiment of the subject invention.

In an embodiment, as illustrated in FIG. 1(b), the SPR based sensing system can comprise a coating 500 having a binding partner that binds to an analyte of interest secreted from living cells. The binding partner can be configured to bind specifically to a biomarker. Moreover, the binding partner is bound or affixed to the SPR sensing surface, such as via a covalent bond or hydrogen bond.

Referring to FIG. 1(b), the SPR sensing surface 100 can be adhered to a support layer 300 capable of transmitting light. In an embodiment, the support layer 300 can comprise glass. In an embodiment, a surface of the support layer 300 contacting the SPR sensing surface 100 is flat or substantially flat. In an embodiment, a surface of the SPR sensing surface 100 contacting the plurality of living cells or being under the plurality of living cells is flat or substantially flat.

In an embodiment, the SPR based sensing system integrated with the cultured living cells can be incorporated into or connected with another apparatus for monitoring and/or analysis of various characteristics of the living cells.

Figure 2:
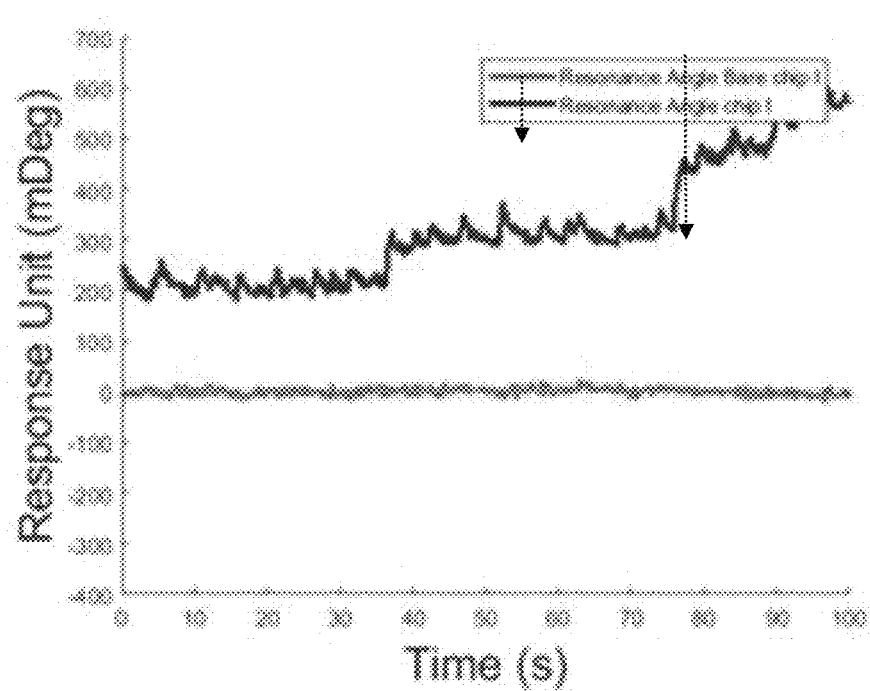
FIG. 2 illustrates responses of resonance angle shift as a function of time for an SPR based sensing surface on which living cardiomyocytes are cultured ("Resonance Angle Chip 1") according to an embodiment of the subject invention, in comparison with responses of resonance angle shift as a function of time of a bare SPR based sensing surface having no living cardiomyocytes cultured on the surface ("Resonance Angle Bare Chip 1").

FIG. 2 illustrates responses of resonance angle shift as a function of time for a SPR based sensing surface on which living cardiomyocytes are cultured ("Resonance Angle Chip 1") according to an embodiment of the subject invention, in comparison with responses of resonance angle shift as a function of time of a bare SPR based sensing surface having no living cardiomyocytes cultured on the surface.

Referring to FIG. 2, from a time of zero seconds to a time of approximately 40 seconds, the response angle shift of the SPR based sensing system maintains at an approximately constant level of about 200 milli-degrees (mdegs). Then, at a time of approximately 40 seconds, the response angle shift of the SPR based sensing system is sharply increased to a higher level of about 300 mdegs and from a time of about 40 seconds to a time of about 78 seconds, the response angle shift of the SPR based sensing system maintains at an approximately constant level of about 300 mdegs.

Next, at a time of approximately 78 seconds, the response angle shift of the SPR based sensing system is again sharply increased to a higher level of about 400 mdegs. Further, from a time of approximately 78 seconds to a time of approximately 100 seconds, the response angle shift of the SPR based sensing system is gradually increased from approximately 400 mdegs to about 600 mdegs.

As illustrated in FIG. 2, in comparison, for a bare SPR based sensing surface having no living cardiomyocytes cultured on the surface ("Resonance Angle Bare Chip 1"), the level of responses of resonance angle shift maintains at an approximately constant level of about zero mdegs for the same time period from zero seconds to approximately 100 seconds.

The measurement results indicate that after the living cardiomyocytes are cultured on the SPR sensing surface, the contractions, expansions, or movements of the living cardiomyocytes causes micro changes of the sensing surface of the SPR based sensing system. The signals represented by resonance angle shift as a function of time show the beating frequency and strength of the living cardiomyocytes in real time.

Figure 3:
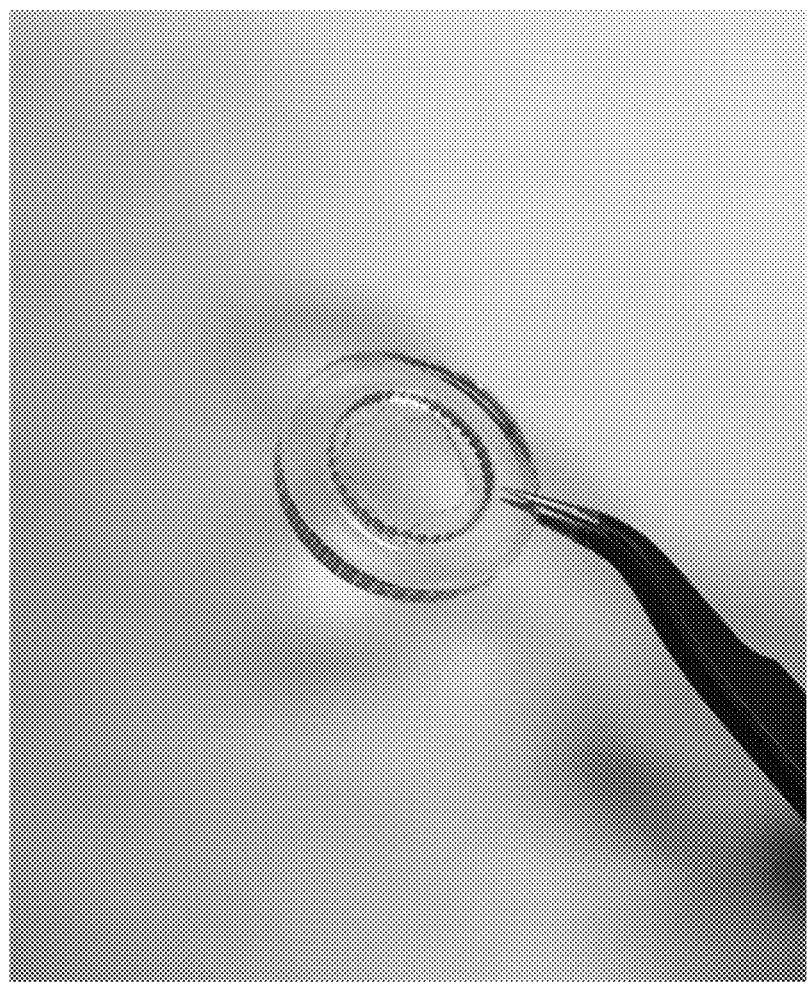
FIG. 3 is an image illustrating a prototype polydimethylsiloxane (PDMS) concentrator for optimizing concentrations of living cells cultured on an SPR based sensing surface, according to an embodiment of the subject invention.
Figures 6A, 6B:
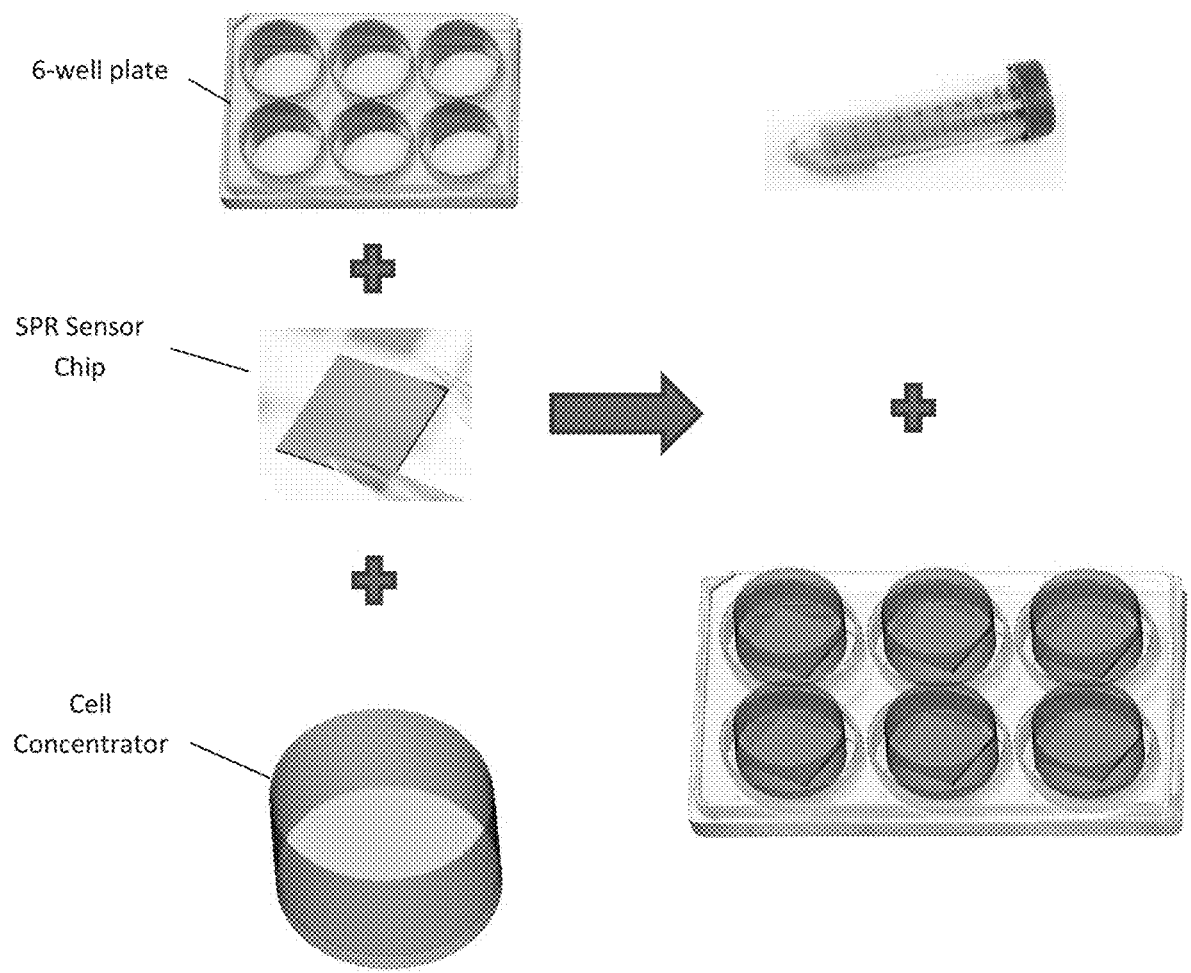
FIGS. 6A and 6B illustrate the process of cell application into SPR for contraction measurements.

In an embodiment, the SPR based sensing system can further comprise a concentrator as shown in FIG. 3. The concentrator can be made of a suitable material, such as, for example, PDMS. In order to achieve the optimal signal read-out for sensing contractions, expansions, or movements of the living cells, the concentrator can be configured to vary the concentrations of the living cells cultured on the SPR sensing surface to determine an optimal concentration for reading the resonance angle shift as a function of time. Referring to FIGS. 6A and 6B, cell cultures can be added to a SPR sensor chip by adding the cell cultures to a well (having the SPR sensor chip) through a concentrator (in the well and) on the SPR sensor chip. As a erson of ordinary skill in the art will understand, the concentrator can also be referred to as a cell concentrator and is an additional component that focuses the cell culture to the center of the sensor chip. This is advantageous for SPR applications, as the cells should be near or on the spot where laser light is incident and refracting back (otherwise the SPR phenomena as the waves dissipate away from the surface will not be as strong to read the cellular micromotions and contractility). The SPR system is therefore capable of receiving cell contraction signals without any further processing non-invasively using this culture technique.

Figure 4:
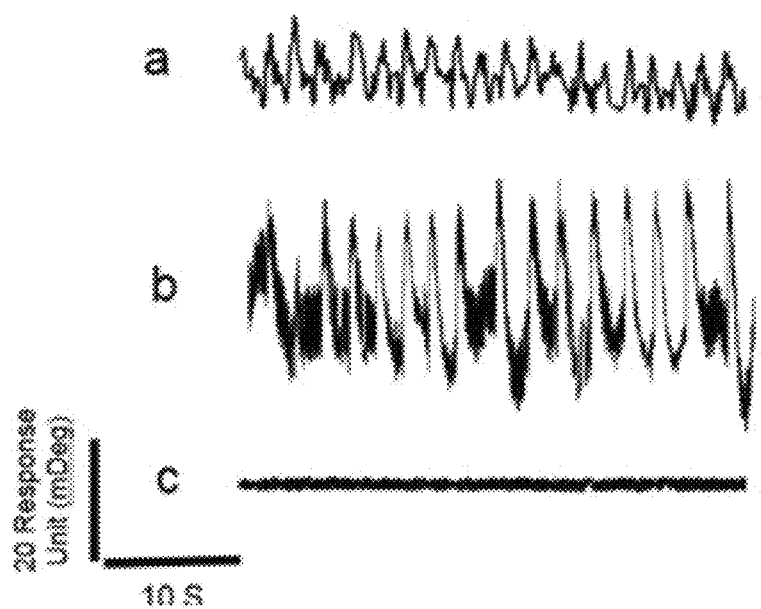
FIG. 4 illustrates responses of resonance angle shift as a function of time for various flow rates of culture medium to show effects of the flow rates of culture medium on signal read-out of rhythmic beating characteristics of living cells, according to an embodiment of the subject invention.

Referring to FIG. 4, the responses of resonance angle shift as a function of time for various flow rates of culture medium are shown according to an embodiment of the subject invention. The measurement results demonstrate the effects of the flow rates of culture medium on signal read-out of the rhythmic beating characteristic of living cells.

FIG. 4 shows three plots of: (a) the time resolved response angle shift of the SPR based sensing system at a flow rate of about 10 μL/minute for the culture medium; (b) the time resolved response angle shift of the SPR based sensing system at a flow rate of about 25 μL/minute for the culture medium; and (c) the time resolved response angle shift of the SPR based sensing system at a flow rate of about 50 μL/minute for the culture medium.

As illustrated in FIG. 4, in an embodiment, the flow rate of about 10 μL/minute is determined to be the optimal flow rate of culture medium to accomplish optimal signal read-out for sensing contractions, expansions, or movements of the living cells, according to an embodiment of the subject invention.

In an embodiment, the SPR based sensing system can sense the beating characteristics of the living cardiomyocytes after the living cardiomyocytes is stimulated by an injection of a stimulator such as, for example, adenosine triphosphate (ATP). In another embodiment, the SPR based sensing system can sense the beating characteristics of the living cardiomyocytes after the living cardiomyocytes is inhibited by an injection of an inhibitor such as, for example, blebbistatin.

Figure 5:
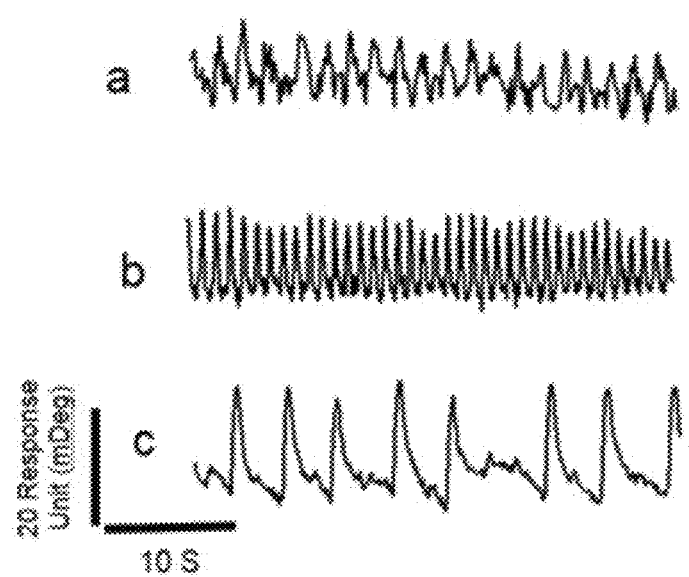
FIG. 5 illustrates responses of resonance angle shift as a function of time for showing effects of injections of biomaterials on the rhythmic beating characteristic of living cells, according to an embodiment of the subject invention.

FIG. 5 shows the effects of adenosine triphosphate (ATP) as a stimulator and blebbistatin as in inhibitor on cardiac activity (beating frequency) of the living cells cultured on the SPR sensing surface, according to an embodiment of the subject invention.

As illustrated in FIG. 5, there are three plots of: (a) the time resolved response angle shift of the SPR based sensing system cultured with the cardiomyocytes having no injection of biomaterials (control group); (b) the time resolved response angle shift of the SPR based sensing system cultured with the cardiomyocytes with an injection of 10 μM ATP as a stimulator; and (c) the time resolved response angle shift of the SPR based sensing system cultured with the cardiomyocytes with an injection of 10 μM blebbistatin as an inhibitor.

In FIG. 5, the plot (a) shows regular cardiac activity (regular beats with baseline frequencies) of cardiomyocytes having no injection of biomaterials (control group). For comparison, the plot (b) of FIG. 5 shows a higher cardiac activity (faster beats with frequencies higher than the baseline frequencies) of the cardiomyocytes, after ATP is injected to the cardiomyocytes as a stimulator. For further comparison, the plot (c) of FIG. 5 shows a lower cardiac activity (slower beats with frequencies lower than the baseline frequencies) of the cardiomyocytes, after blebbistatin is injected to the cardiomyocytes as an inhibitor.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A surface plasmon resonance (SPR) based sensing system for sensing contractions, expansions, movements, or a combination thereof of living cells, the system comprising:
   an SPR sensing surface that generates SPR upon stimulation by incident light and senses contractions, expansions, movements, or a combination thereof of the living cells on and directly contacting the SPR sensing surface;
   a cell concentrator disposed over the SPR sensing surface, that concentrates the living cells on the SPR sensing surface; and
   at least one cell culture module that cultures the living cells to be disposed on the SPR sensing surface.

2. The system according to claim 1, the SPR sensing surface comprising a metallic surface.

3. The system according to claim 2, the metallic surface comprising gold.

4. The system according to claim 1, further comprising a support layer capable of transmitting light,
   the SPR sensing surface being adhered to the support layer.

5. The system according to claim 1, further comprising at least one controller that determines a flow rate of a culture medium contacting the living cells cultured on the SPR sensing surface for sensing contractions, expansions, movements, or a combination thereof of the living cells.

6. The system according to claim 1, further comprising at least one controller that determines a cell culturing condition of the at least one cell culture module for sensing contractions, expansions, movements, or a combination thereof of the living cells.

7. The system according to claim 1, the living cells comprising living cardiomyocytes.

8. The system according to claim 1,
   the system further comprising a coating coated on the SPR sensing surface for performing real-time analysis of the at least one analyte secreted from the living cells.

9. The system according to claim 8, the at least one cell culture module releasing at least one analyte secreted from the living cells onto the SPR sensing surface to be sensed by the SPR sensing surface.

10. The system according to claim 8, the coating comprising a binding partner that binds to the at least one analyte secreted from the living cells, and
    the binding partner binding specifically to a biomarker.

11. A method of sensing contractibility, movements, or both of living cells by a surface plasmon resonance (SPR) based sensing system, the SPR based sensing system comprising:
    an SPR sensing surface that generates SPR upon stimulation by incident light;
    a cell concentrator disposed over the SPR sensing surface, that concentrates the living cells on the SPR sensing surface; and
    at least one cell culture module for culturing the living cells,
    the method comprising:
    culturing, by the at least one cell culture module, the living cells to be disposed on the SPR sensing surface;
    adding the cultured living cells to the SPR sensing surface through the cell concentrator, such that the cultured living cells are in direct contact with the SPR sensing surface; and
    sensing, by the SPR sensing surface, contractions, expansions, movements, or a combination thereof of the cultured living cells directly contacting the SPR sensing surface.

12. The method according to claim 11, the SPR based sensing system further comprising at least one controller, the method further comprising:
    determining, by the at least one controller, an optimal a concentration of the living cells cultured on the SPR sensing surface for sensing contractions, expansions, movements, or a combination thereof of the living cells.

13. The method according to claim 11, the SPR based sensing system further comprising at least one controller, the method further comprising:
    determining, by the at least one controller, a flow rate of a culture medium contacting the living cells on the SPR sensing surface for sensing contractions, expansions, movements, or a combination thereof of the living cells.

14. The method according to claim 11, the SPR based sensing system further comprising at least one controller, the method further comprising:
    determining, by the at least one controller, a cell culture condition(s) of the at least one cell culture module for sensing contractions, expansions, movements, or a combination thereof of the living cells.

15. The method according to claim 11, the step of sensing by the SPR sensing surface comprising:
    sensing contractions, expansions, movements, or a combination thereof of the living cells, after a biomaterial is added to the living cells.

16. The method according to claim 15, the biomaterial comprising a stimulator.

17. The method according to claim 16, the stimulator comprising adenosine triphosphate (ATP).

18. The method according to claim 15, wherein the biomaterial comprising an inhibitor.

19. A surface plasmon resonance (SPR) based sensing system for sensing contractions, expansions, movements, or a combination thereof of living cells, the system comprising:
    an SPR sensing surface that generates SPR upon stimulation by incident light and senses contractions, expansions, movements, or a combination thereof of the living cells on the SPR sensing surface;
    at least one cell culture module that cultures the living cells to be disposed on the SPR sensing surface;
    a support layer capable of transmitting light, the SPR sensing surface being adhered to the support layer;
    a cell concentrator disposed over the SPR sensing surface, that concentrates the living cells on the SPR sensing surface; and
    at least one controller that determines both: a flow rate of a culture medium contacting the living cells cultured on the SPR sensing surface for sensing contractions, expansions, movements, or a combination thereof of the living cells; and a cell culturing condition of the at least one cell culture module for sensing contractions, expansions, movements, or a combination thereof of the living cells,
    the SPR sensing surface comprising a metallic surface,
    the metallic surface comprising gold,
    the living cells comprising living cardiomyocytes, the system further comprising a coating coated on the SPR sensing surface for performing real-time analysis of the at least one analyte secreted from the living cells, the at least one cell culture module releasing the at least one analyte secreted from the living cells is released onto the SPR sensing surface to be sensed by the SPR sensing surface, the coating comprising a binding partner that binds to the at least one analyte secreted from the living cells, and the binding partner binding specifically to a biomarker.

* * * * *